US009056073B2

(12) United States Patent
Varga et al.

(10) Patent No.: US 9,056,073 B2
(45) Date of Patent: Jun. 16, 2015

(54) VACCINE COMPRISING LACTOBACILLI FOR TREATING PROSTATE INFLAMMATION AND BENIGN PROSTATE HYPERPLASIAS

(75) Inventors: Gyule Varga, Kazincbarcika (HU); Ottilia Ujhelyi, Budapest (HU); Tamás Újhelyi, Budapest (HU); Erike Lázár, Budapest (HU); József Bartus, Sajagalgoc (HU)

(73) Assignee: VAKCINA KFT, Sajógalgóc (HU)

( * ) Notice: Subject to any disclaimer, the term of this patent is extended or adjusted under 35 U.S.C. 154(b) by 461 days.

(21) Appl. No.: 13/049,344

(22) Filed: Mar. 16, 2011

(65) Prior Publication Data

US 2011/0243990 A1    Oct. 6, 2011

Related U.S. Application Data

(63) Continuation of application No. 12/077,780, filed on Mar. 21, 2008, now abandoned, which is a continuation of application No. 10/130,823, filed as application No. PCT/HU00/00122 on Nov. 23, 2000, now abandoned.

(30) Foreign Application Priority Data

Nov. 25, 1999   (HU) .................................. 9904408

(51) Int. Cl.
| | | |
|---|---|---|
| A61K 39/02 | (2006.01) | |
| A61K 39/00 | (2006.01) | |
| A61K 39/38 | (2006.01) | |
| A01N 63/00 | (2006.01) | |
| A61K 39/09 | (2006.01) | |
| A61K 38/00 | (2006.01) | |
| A61K 35/74 | (2006.01) | |
| A61K 39/39 | (2006.01) | |

(52) U.S. Cl.
CPC ................. *A61K 39/09* (2013.01); *A61K 38/00* (2013.01); *A61K 2039/552* (2013.01); *A61K 39/00* (2013.01); *A61K 35/747* (2013.01); *A61K 35/74* (2013.01); *A61K 39/39* (2013.01); *A61K 2039/521* (2013.01)

(58) Field of Classification Search
CPC . A61K 38/00; A61K 39/00; A61K 2039/552; A61K 35/74; A61K 35/747
See application file for complete search history.

(56) References Cited

U.S. PATENT DOCUMENTS 4,238,478 A    12/1980   Stojkovic ........................ 424/92

FOREIGN PATENT DOCUMENTS

| DE | 195 22472 | 1/1997 |
|---|---|---|
| WO | 99/10476 | 3/1999 |
| WO | 99/42568 | 8/1999 |
| WO | WO 99/42568 | 8/1999 |
| WO | 00/78322 | 12/2000 |

OTHER PUBLICATIONS

Ujhelyi et al (Role of *Lactobacillus* in Urogenital Inflammations and their Treatment with Vaccination (Symposium cum participation internationali de Biacenosi vaginae 14-15 okt. 1983 Smolenice).*
Krieger et al (World Journal of Urology, Spinger-Verlag Apr. 24, 2003).*
Lazer et al (Reduction of the Ratio of low-weight neonates by *Lactobacillus* vaccination during pregnancy, Orvosi Hetilap (Physicians Weekly) 37:2263-2268, 1981).*
Embley et al (International Journal of Systematic Bacteriology, Jul. 1989, Vo. 39, No. 3, p. 368-370).*
K. Ujhelyi et al., "Role of *Lactobacillus* in Urogenital Inflammations and Their Treatment with Vaccination", Symposium cum participatione internationalis de Biocenosi, Vaginae, Smolenie 1983 (English Translation).
K. Ujhelyi et al., "Role of *Lactobacillus* in Urogenital Inflammations and Their Treatment with Vaccination", Symposium cum participatione internationalis de Biocenosi, Vaginae, Smolenie 1983. Annex 4 to the renewal of marketing authorization No. OGYI-T-20173/01-02, Budapest, Jul. 19, 2006.
Karkut G., Wirkung einer *Lactobazillus*-Immuntherapie auf die Genitalinfektion der Frau (SolcoTrichovac/Gynatren), *Geburtsh. u. Frauenheilk*, 44:311 (1984).
Lázár, E., et al., *Magyar Nöorvosok Lapja* (Journal of Hungarian Gynaecologists), 51:353-356 (1988) (with English translation).
Lázár E., et al., Decreasing the ratio of neonates with small weight by lactobact vaccination of pregnant women (in Hungarian), *Orvosi Hetilap* (Physicians Weekly), 37:2263-2268 (1981) (with English translation).
Újhelyi K., et al., The Trichomonas syndrome I (in Hungarian), *Magyar Nöorvosok Lapja* (Journal of Hungarian Gynaecologists), 36:433-442 (1973) (with English translation).
John N. Krieger, et al., Epidemiology of prostatitis: new evidence for a world-wide problem, World Journal of Urology, 10.1007/s00345-003-0329-0, Apr. 24, 2003.
Litschgi et al, Fortscher Med, 1980, 98(41), p. 1624-1627.
Gardner et al, Arch Pathol Lab Med, vol. 110, May 1996.
Gleason et al (Journal of Urology, 1993, vol. 149, No. 6, p. 1586-1592) (Abstract only).

(Continued)

*Primary Examiner* — Gary Nickol
*Assistant Examiner* — Lakia Tongue
(74) *Attorney, Agent, or Firm* — Choate, Hall & Stewart LLP; Andrea L. C. Reid; Danielle M. Nihan

(57) ABSTRACT

The invention relates to vaccines for treating prostate inflammation and benign prostate hyperplasias (stages I and II) comprising *Lactobacillus* strains in an inactivated form and carriers and/or excipients commonly used in vaccine preparations.

4 Claims, No Drawings

(56) References Cited

OTHER PUBLICATIONS

Gardner et al (Arch Pathol Lab Med, vol. 110, May 1996).
Cannon et al (Eur. J. Clin. Microbiol. Infect. Dis (2005), 24:31-40).
Pattman et al (Int J STD AIDS, Jul.-Aug. 1994;5(4):299(Abstract).
Alderete (Genilourin Med. Apr. 1988;64(2):118-23(Abstract).
GYNEVAC ((home page) Retrieved from the Internet <URL: www.gynevac.hu.com/infoeng.hmtl >).
Alderete (Genitourin Med, Apr. 1988; 64(2):118-23).
Gynatren available at http://www.gynatren.de/.
Gynevac available at (http://www.gynevac.hu/).
Cannon et al (Eur. J. Clin. Microbiol. Infect. Dis (2005), 24 :31-40).

\* cited by examiner

VACCINE COMPRISING LACTOBACILLI FOR TREATING PROSTATE INFLAMMATION AND BENIGN PROSTATE HYPERPLASIAS

CROSS-REFERENCE TO RELATED APPLICATIONS

This application is a Continuation of U.S. patent application Ser. No. 12/077,780, filed Mar. 21, 2008 now abandoned, which is a Continuation of U.S. patent application Ser. No. 10/130,823, filed Sep. 16, 2002 now abandoned, which is a United States National Phase patent application under 35 U.S.C. §371 of PCT/HU00/00122, filed Nov. 23, 2000, which claims priority to Hungarian patent application P9904408, filed Nov. 25, 1999, the entirety of each of which is hereby incorporated herein by reference.

SEQUENCE LISTING

In accordance with 37 CFR 1.52(e)(5), a Sequence Listing in the form of a text file (entitled "Sequence_Listing.txt," created on Nov. 10, 2014, and 4 kilobytes in size) is incorporated herein by reference in its entirety.

FIELD OF INVENTION

The present invention relates to a vaccine comprising *Lactobacillus* strains useful in treating prostate inflammation and benign prostate hyperplasias (stages I and II).

BACKGROUND OF THE INVENTION

The pathogenecity of certain *Lactobacillus* strains has been reported in 1938 [F. Marshall: Der Döderleinische *Bacillus vaginalis* als Endokarditiserreger, *Zentr. Bact. Parasit. Kde. I. Abt. Orig.*, 141:153-159 (1938); E. Biocca és A. Sepilli: Human infections caused by *lactobacilli*, *J. Inf. Dis.*, 81:112-115 (1947); W. Sims: A pathogenic *Lactobacillus*, *J. Path. Bact.*, 87:99-105 (1964); B. Rosan and B. F. Hammond: Toxicity of *Lactobacillus casei*, *J. Dent. Res.*, 44:783-787 (1965); M. E. Sharpe, L. R. Hill and S. P. Lapage: Pathogenic *lactobacilli*, *J. Med. Microbiol.*, 6, 281-286 (1973).

G. Wied reported in 1952 [ZbI. Bact., 160:413 (1952)] that certain *Lactobacillus* strains show mucous membrane damaging activity. Rosan and Hammond [1965, ibid.] reported that, with *Lactobacillus* strains strongly pathogenic to mice, intradermal inoculation of bacteria both in living and in thermally inactivated states causes necrosis on the back of rabbits.

K. Újhelyi has found that necrosis can be induced also by *Lactobacillus* strains cultivated from vagina. Based on his observation, it can be stated that the body of the bacterium contains a toxin which is responsible for damaging the epithelia [Újhelyi K. et al.: Role of *Lactobacillus* in urogenital inflammations and their treatment with vaccination, Symposium cum participatione internationalis de Biocenosi Vaginae, Smolenie, 1983]. Certain strains, injected intradermally to the back of rabbits, cause necrosis of smaller or larger areas, while others cause necrosis only in higher concentration or do not cause necrosis at all. K. Újhelyi has found that rabbits can be immunized by vaccination against the necrotic effect. He vaccinated rabbits intramuscularly with vaccine produced from certain *Lactobacillus* strains. Six weeks later, he intradermally administered cell-suspensions prepared from strains that have been shown previously to be necrotic, and observed that necrosis was not caused or was only caused in a lesser degree than in the case of non-vaccinated rabbits.

Furthermore, K. Újhelyi has found that *Trichomonas vaginalis* contributes to the rise in vaginal pH by consuming lactic acid produced by *Lactobacillus* strains in the vagina, thereby promoting the over-proliferation of *Lactobacillus* strains. Consequently toxin is present in higher concentration which, by damaging the mucous membrane, causes cell necrosis.

Furthermore, it is known that *Lactobacillus* strains, because of their receptor inhibiting and antibiotic activity as well as pH-modifying effect, are antagonistic to pyogenic microorganisms [Reddy et al.: Natural antibiotic activity of *Lactobacillus*, *Dairy Prod. J.* 18:15-22 (1983); Salminen et al.: Lactic acid bacteria in the gut in normal and disordered states, *Dig. Dis.*, 10:227-238 (1992)].

Recently, it has been shown that *Lactobacillus* strains can bind directly to T-lymhocytes since both the T-helper and T-killer cells have specific receptors for *Lactobacillus* strains. Furthermore, *Lactobacillus* strains promote the gamma-interferon production of the lymphocytes and the cytotoxic activity of the natural killer cells [De Simone C., et al.: Enhancement of immune response of murine Peyer's pothes by a diet supplemented with yoghurt, *J. Immunopharmacol.*, 1:87-95 (1987)]. It has been shown that *Lactobacillus* strains aspecifically increase the production of IgM and IgG [Blocksma et al.: Adjuvant activity of *lactobacilli*, different effects of viable and killed bacteria, *Clin. Exp. Immunol.*, 37:367-373]. Additionally, under experimental conditions, *Lactobacillus* strains show antitumour and macrophage-activating activity [Kato I. et al.,: Antitumor activity of *Lactobacillus casei* in mice, Gann, 72:517-523 (1983); Oda M. et al.: Antitumor polysaccharide from *Lactobacillus* sp., *Agric Biol. Chem.*, 47:1623-1627 (1983)]. H. Rüttgers has found that immunostimulation by *Lactobacillus* strains causes a significant long-lasting rise in secretory immunoglobulin level in the vagina [Bacterial vaginitis: Protection against infection and secretory immunoglobulin levels in the vagina after immunization therapy with Gynatren, *Gynecol. Obstet Invest*, 26:240-249 (1988)].

Újhelyi of al. [1983, ibid.] used parenterally administered *Lactobacillus* strains for aspecific immunostimulation and observed that the *Lactobacillus* strains used, in contrast to other aspecific immunostimulation (e.g. by BCG, endotoxins etc.), show protective effect against certain bacterial toxins. This applies especially to toxic *Lactobacillus* strains.

In trials carried out with vaccines (Gynevac®, Gynatren®, Solco Trichovac®) made of strains cultured by Újhelyi it has been demonstrated that immunostimulation by *Lactobacillus* strains, in contrast to other therapeutic treatments, restores the biological balance of the vagina, normalizes the pH, decreases the number of pathogenic bacteria, and contributes to the propagation of Döderlein-flora (a mixed population of *Lactobacillus* strains capable of being cultivated from vaginal specimens). It is an accepted fact that inflammatory diseases of the vagina caused by bacterial and *Trichomonas* infections can be cured in this way more successfully than by other therapy and that such inflammatory conditions are a major cause of premature births. Therefore, the frequency of premature births can also be decreased by such therapy [see e.g. in Genitalinfektion der Frau (SolcoTrichovac/Gynatren), *Geburtsch. u. Frauenheilk*, 44:311 (1984); E. Lázár, Gy. Varga, I. Institoris and K. Újhelyi: Investigating the factors, especially vaccination with *lactobacilli*, influencing the premature births, in Kazincbarcika (in Hungarian), *Magyar Nöorvosok Lapja* (Journal of Hungarian Gynaecologists), 51:353-356 (1986); E. Lázár, Gy. Varga, I. Institoris and K. Újhelyi: Decreasing the ratio of neonates with small weight by lactobact vaccination of pregnant women (in Hungarian), *Orvosi Hetilap* (Physicians Weekly), 37:2263-2268 (1981), Rüttgers, 1988, ibid., K. Újhelyi, Gy. Philipp, Gy. Plank and V. Sági: The *Trichomonas* syndrome I (in Hungarian), *Magyar Nöorvosok Lapja* (Journal of Hungarian Gynaecologists), 36:433-442 (1973); Sharon et al., *New England Journal*, Dec. 28, 1995.].

More than 50% of men aged 50 or more suffer from prostate hyperplasia and/or prostate inflammation. In spite of numerous known and utilized therapies, treatment is often unsuccessful. Taking into consideration the known and generally accepted pathogenesis, it could not be supposed that such diseases can be healed with vaccines comprising *Lactobacillus* strains successfully.

The inventors of the present invention have, however, found that conditions in the prostate are favorable to the proliferation of *Lactobacillus* strains and that pathogenic *lactobacilli* can often be cultivated from patients suffering from chronic prostate inflammation and/or prostate hyperplasia. On this basis, therapeutic utilization of vaccines comprising *Lactobacillus* strains for treating such patients has been achieved.

DISCLOSURE OF THE INVENTION

The invention relates to vaccines for treating prostate inflammations and benign prostate hyperplasias (stages I and II) comprising *Lactobacillus* strains in inactivated form and carriers and/or excipients commonly used in vaccine preparations.

In another aspect, the invention relates to the use of *Lactobacillus* strains for producing vaccines capable of treating prostate inflammation and benign prostate hyperplasias (stages I and II).

In a further aspect, the invention relates to the use of *Lactobacillus* strains for treating patients suffering from prostate inflammation and benign prostate hyperplasias (stages I and II).

Furthermore, the invention relates to a method of treating patients suffering from prostate inflammation and benign prostate hyperplasias (stages I and II) comprising administering an effective dose of a strain-suspension of *Lactobacillus* strains intramuscularly to a patient in need of such treatment.

In an embodiment of the method of the invention, the strain-suspension of *Lactobacillus* strains comprises a mixed population of the said strains in inactivated form.

The *lactobacilli* used in the vaccine of the invention are *Lactobacillus* strains used in the above-said vaccines Gynevac®, Gyantren® and SolcoTrichovac® that previously have been cultivated from women suffering from gynecologic inflammations of bacterial origin. The single cultivated strains can be use per se or in the form of a blend of the strains.

The vaccine of the invention can be produced by methods commonly used for preparing vaccines. Advantageously, the cultivated strains are stored in lyophilized form, then, before use, they are propagated by culturing in Man-Rogosa-Sharpe medium at 45° C.

The composition of the said medium and the preparation method are set forth below.

To 2300 ml of sterile water the following components are added sequentially, after dissolving the previously added component:

| | |
|---|---|
| Bactotripton (Raenal) | 30 g |
| Lablemko (Reanal) | 30 g |
| $K_2HPO_4$ | 6 g |
| triammonium citrate | 6 g |
| sodium acetate | 15 g |
| glucose | 30 g |
| lactose | 30 g |
| maltose | 9 g |
| yeast extract (Reanal) | 15 g |
| Tween 80 | 3 ml |
| Salt solution (composition see below) | 15 ml |

The obtained solution is adjusted to 3000 ml by the addition of sterile water, filtered on G4 filter, bottles in smaller volumes and sterilized at 121° C.

The composition of the above-said salt solution is as follows: 28.75 g of $MgSO_4$-$7H_2O$, 6 g of $MnSO_4$-$2H_2O$ and 1.7 of $FeSO_4$-$7H_2O$ dissolved in 250 ml of sterile water.

After culturing, the cells are harvested by centrifuging and are suspended in physiological saline solution and treated with formaldehyde. The inactivated cells are harvested and resuspended in physiological saline solution. The level of dilution is adjusted on the basis of the protein content of the suspension. The protein content of the vaccine (suspension) of the invention is at least 0.08 mg/ml, and may be up to 1 mg/ml or more, preferably from about 0.08 to about 0.32 mg/ml, more preferably about 0.16 mg/ml.

The dosage of the vaccine of the invention and the frequency of the administration depend on the conditions of the patient and the severity of the symptoms to be treated. The precise dose and frequency of administration should be specified by the practicing physician. During treatment, it is advantageous if the vaccine is administered intramuscularly in a volume of 1 ml, once a week for five weeks.

The following example is given for the purpose of illustration of the invention without the intention of limiting of the scope claimed.

EXAMPLE

Investigations were carried out with the vaccine of the invention by administering same to patients with a diagnosis of prostate inflammation and/or prostate hyperplasias (stages I and II). The patients were administered intramuscularly 1 ml of a vaccine comprising *Lactobacillus* strains of the invention once weekly for 5 weeks, without any other medical treatment. The results of the control examination carried out after this cure are summarized in the following Tables.

Number of the treated patients: 127
Diagnosis: prostate hyperplasia stages I and II

| Condition of the patients | Time elapsed after the treatment | | |
|---|---|---|---|
| | 4 to 8 weeks | 2 to 4 months | 6 months |
| Healed | 52 (40.94%) | Worsening of the condition was not observed in any of the patients. | 60% of 94 examined patients were symptom-free. |
| Improved | 47 (37.0%) | | |
| Unchanged | 28 (22.0%) | | |
| Worsened | 0 | | |

Number of the treated patients: 168
Diagnosis: prostate inflammation

| Condition of the patients | Time elapsed after the treatment | | |
|---|---|---|---|
| | 4 to 8 weeks | 2 to 4 months | 6 months |
| Healed | 76 (45.23%) | Worsening of the condition was not observed in any of the patients. | 70% of 79 examined patients were symptom-free. |
| Improved | 61 (36.31%) | | |
| Unchanged | 31 (18.45%) | | |
| Worsened | 0 | | |

As can be seen in the above Tables, a significant ratio of the patients were healed or their conditions improved essentially.

The invention claimed is:

1. A method for treating a prostate disorder selected from prostate inflammation, benign prostate hyperplasia stage I, or benign prostate hyperplasia stage II in a male patient in need thereof, comprising administering to said patient a vaccine comprising inactivated *Lactobacillus* strains, wherein said inactivated *Lactobacillus* strains are a *Lactobacillus reuteri* strain, a first *Lactobacillus fermentum* strain, a second *Lactobacillus fermentum* strain, a third *Lactobacillus fermentum* strain and a fourth *Lactobacillus fermentum* strain, and wherein the *Lactobacillus reuteri* strain is characterized in that PCR amplification of the genomic DNA of said *Lactobacillus reuteri* strain using a first primer having the nucleotide sequence of SEQ ID NO: 1 and a second primer having the nucleotide sequence of SEQ ID NO: 2 produces a 98 bp amplification product having the nucleotide sequence of SEQ ID NO: 11, the first *Lactobacillus fermentum* strain is characterized in that PCR amplification of the genomic DNA of said first *Lactobacillus fermentum* strain using a first primer having the nucleotide sequences of SEQ ID NO: 3 and a second primer having the nucleotide sequence of SEQ ID NO: 4 produces a 146 bp amplification product having the nucleotide sequence of SEQ ID NO: 12, the second *Lactobacillus fermentum* strain is characterized in that PCR amplification of the genomic DNA of said second *Lactobacillus fermentum* strain using a first primer having the nucleotide sequences of SEQ ID NO: 5 and a second primer having the nucleotide sequence of SEQ ID NO: 6 produces a 139 bp amplification product having the nucleotide sequence of SEQ ID NO: 13, the third *Lactobacillus fermentum* strain is characterized in that PCR amplification of the genomic DNA of said third *Lactobacillus fermentum* strain using a first primer having the nucleotide sequences of SEQ ID NO: 7 and a second primer having the nucleotide sequence of SEQ ID NO: 8 produces a 227 bp amplification product having the nucleotide sequence of SEQ ID NO: 14, and the fourth *Lactobacillus fermentum* strain is characterized in that PCR amplification of the genomic DNA of said fourth *Lactobacillus fermentum* strain using a first primer having the nucleotide sequences of SEQ ID NO: 9 and a second primer having the nucleotide sequence of SEQ ID NO: 10 produces a 150 bp amplification product having the nucleotide sequence of SEQ ID NO: 15.

2. The method according to claim 1, wherein the vaccine is administered intramuscularly.

3. The method according to claim 1, wherein the prostate disorder is benign prostate hyperplasia stage I or benign prostate hyperplasia stage II.

4. The method according to claim 1, wherein the prostate disorder is prostate inflammation.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 1
acagtcttct cgacaaggcg                                               20

<210> SEQ ID NO 2
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 2
agaactctag cttcgcgtcg                                               20

<210> SEQ ID NO 3
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 3
cgttactcag gccatccaat t                                             21

<210> SEQ ID NO 4
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 4
ccaaggctaa ctggtgattg at                                            22

<210> SEQ ID NO 5
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 5
tgcaaagcaa gtgatggaac                                               20

<210> SEQ ID NO 6
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 6
cttagcggcc ttagcgaca                                                19

<210> SEQ ID NO 7
<211> LENGTH: 18
<212> TYPE: DNA
<213> ORGANISM: Artificial Sequence

```
<220> FEATURE:
<223> OTHER INFORMATION: chemically synthesized oligonucleotide

<400> SEQUENCE: 7
ctgaccctga ccgtccgt                                                    18

<210> SEQ ID NO 8
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 8
aagcgggtaa ttaagtgggg                                                  20

<210> SEQ ID NO 9
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 9
aatcatccta ttggacgagc c                                                21

<210> SEQ ID NO 10
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 10
aagaccacct gatccatttt gt                                               22

<210> SEQ ID NO 11
<211> LENGTH: 98
<212> TYPE: DNA
<213> ORGANISM: Artificial Sequence
<220> FEATURE:
<223> OTHER INFORMATION: chemically synthesized oligonucleotide

<400> SEQUENCE: 11
acagtcttct cgacaaggcg gttggctaaa ctaaggcgga gtcacgggct gattatcgtt       60
cagacgtgag ccttgtgacg acgcgaagct agagttct                              98

<210> SEQ ID NO 12
<211> LENGTH: 146
<212> TYPE: DNA
<213> ORGANISM: Artificial Sequence
<220> FEATURE:
<223> OTHER INFORMATION: chemically synthesized olignucleotide

<400> SEQUENCE: 12
cgttactcag gccatccaac tcctggaacg tgaatttgac gtccaattgg tcgacgttgc       60
ccgtggccgg cggggatga agatcacccg ggctggtcag ttactttacc aagcggcgga      120
ccggatcaat caccagttag ccttgg                                          146

<210> SEQ ID NO 13
<211> LENGTH: 139
<212> TYPE: DNA
<213> ORGANISM: Artificial Sequence
<220> FEATURE:
```

-continued

```
<223> OTHER INFORMATION: chemically synthesized oligonucleotide

<400> SEQUENCE: 13
cttagcggcc ttagcgatac cctttcacg aaggtaatcc attgccttgt ccatgtcacc        60
ttcactagca acgagggcct tcttggcgtc catgatcccg gcaccggact tcttgcgcag      120
ttccatcact tgctttgca                                                    139

<210> SEQ ID NO 14
<211> LENGTH: 227
<212> TYPE: DNA
<213> ORGANISM: Artificial Sequence
<220> FEATURE:
<223> OTHER INFORMATION: chemically synthesized oligonucleotide

<400> SEQUENCE: 14
ctgaccctga ccgtccatcc tgaaccgggt gacgccaccg tagcgacttc cgaagagcca       60
ctgacgattg tctacgagga tgacaactgg ttggtcgtga acaaaccagt ggggtagcc      120 tcggttcccg gccccacgt ggtcaacggg acgatcctaa accgggtgaa gggctaccta      180
gtggccaagg acgcgccgga tctgcgcccc cacttaatta cccgctt                    227

<210> SEQ ID NO 15
<211> LENGTH: 150
<212> TYPE: DNA
<213> ORGANISM: Artificial Sequence
<220> FEATURE:
<223> OTHER INFORMATION: chemically synthesized oligonucleotide

<400> SEQUENCE: 15
aagaccacct gatccatttt atcgacccc tggaggtggt gagtaatcca gattagggtc       60
ttgccctgta actgggtcat aaaggtgtct aagacctcct gttccgtaac cgggtccagc    120
ccgaccgttg gctcgtccaa taggatgatt                                      150
```